US012749580B2

(12) United States Patent
Hashemi et al.

(10) Patent No.: US 12,749,580 B2
(45) Date of Patent: Sep. 29, 2026

(54) SYSTEMS, METHODS AND DEVICES FOR PREDICTING PERSONALIZED BIOLOGICAL STATE, PREDICTING PERSONALIZED BEHAVIOR, AND RECOMMENDING PERSONALIZED BEHAVIOR WITH MODELS PRODUCED WITH META-LEARNING

(71) Applicant: January, Inc., Menlo Park, CA (US)

(72) Inventors: Noosheen Hashemi, Menlo Park, CA (US); Mark Woodward, San Carlos, CA (US); Hootan Rashtian, Vancouver (CA); Ashkan Dehghani Zahedani, Redwood City, CA (US); Saransh Agarwal, San Francisco, CA (US)

(73) Assignee: JANUARY, INC., Menlo Park, CA (US)

( * ) Notice: Subject to any disclaimer, the term of this patent is extended or adjusted under 35 U.S.C. 154(b) by 185 days.

(21) Appl. No.: 17/737,850

(22) Filed: May 5, 2022

(65) Prior Publication Data

US 2022/0359079 A1 Nov. 10, 2022

Related U.S. Application Data

(60) Provisional application No. 63/185,283, filed on May 6, 2021.

(51) Int. Cl.
*G16H 50/20* (2018.01)
*G16H 20/30* (2018.01)
(Continued)

(52) U.S. Cl.
CPC ............. *G16H 50/20* (2018.01); *G16H 20/30* (2018.01); *G16H 20/60* (2018.01); *G16H 50/30* (2018.01); *G16H 50/70* (2018.01)

(58) Field of Classification Search
CPC ............ G06N 3/08; G06N 3/04; G06N 3/084; G06N 3/0985; G06N 7/00; G16H 50/50; G16H 50/70; G16H 20/60; A61B 5/1495
(Continued)

(56) References Cited

U.S. PATENT DOCUMENTS

2009/0163776 A1* 6/2009 Inbar ...................... G16H 50/70 600/301
2016/0314243 A1* 10/2016 Sugimoto .............. G06N 3/126
(Continued)

FOREIGN PATENT DOCUMENTS

WO WO-2020008192 A2 1/2020
WO WO-2020037244 A1 2/2020
WO WO-2020230123 A1 11/2020

OTHER PUBLICATIONS

Fettke, et al.: Combined Cell-free DNA and RNA Profiling of the Androgen Receptor: Clinical Utility of a Novel Multianalyte Liquid Biopsy Assay for Metastatic Prostate Cancer. Eur. Urol. 78(2):173-180 (2020). doi: 10.1016/j.eururo.2020.03.044. Epub May 30, 2020.
(Continued)

*Primary Examiner* — Alaaeldin M. Elshaer
(74) *Attorney, Agent, or Firm* — Wilson Sonsini Goodrich & Rosati

(57) ABSTRACT

An exemplary method can include using meta-learning on various biological and/or behavior related data sets to generate model parameters for predicting biological and/or behavior predictions. Meta-learned model parameters can configure learning algorithms to rapidly train model/functions for predicting user biological and/or behavioral responses. In some embodiments, recommendations can be generated for a user based on predicted biological and/or one or more behavioral predictions. Corresponding systems are also disclosed.

13 Claims, 14 Drawing Sheets

(51) Int. Cl.

| | |
|---|---|
| ***G16H 20/60*** | (2018.01) |
| ***G16H 50/30*** | (2018.01) |
| ***G16H 50/70*** | (2018.01) |

(58) Field of Classification Search
USPC .......................................................... 705/2, 3
See application file for complete search history.

(56) References Cited

U.S. PATENT DOCUMENTS

| | | | | |
|---|---|---|---|---|
| 2018/0039731 | A1 | 2/2018 | Szeto | |
| 2019/0197360 | A1* | 6/2019 | Kraus | G06F 18/217 |
| 2019/0303786 | A1 | 10/2019 | Hunt et al. | |
| 2019/0379589 | A1* | 12/2019 | Ryan | G06N 3/084 |
| 2020/0375549 | A1* | 12/2020 | Wexler | G16H 50/20 |
| 2021/0104173 | A1* | 4/2021 | Pauley | G16H 20/10 |
| 2021/0327540 | A1* | 10/2021 | Schobel | G16H 50/20 |
| 2022/0039756 | A1* | 2/2022 | Mikhno | A61B 5/7275 |
| 2022/0323855 | A1* | 10/2022 | Khare | A63F 13/65 |

OTHER PUBLICATIONS

Kohli, et al.: Clinical and genomic insights into circulating tumor DNA-based alterations across the spectrum of metastatic hormone-sensitive and castrate-resistant prostate cancer. EBioMedicine. 54:102728 (2020). doi: 10.1016/j.ebiom.2020.102728.
PCT/US2022/027787 International Search Report and Written Opinion dated Sep. 2, 2022.
EP22799558.6 Extended European Search Report dated Feb. 3, 2025.

* cited by examiner

SYSTEMS, METHODS AND DEVICES FOR PREDICTING PERSONALIZED BIOLOGICAL STATE, PREDICTING PERSONALIZED BEHAVIOR, AND RECOMMENDING PERSONALIZED BEHAVIOR WITH MODELS PRODUCED WITH META-LEARNING

CROSS-REFERENCE

This application claims priority to U.S. Provisional Patent Application No. 63/185,283 filed on May 6, 2021, which application is entirely incorporated herein by reference in its entirety for all purposes.

BACKGROUND

The present disclosure relates generally to systems and methods for predicting biological states with a statistical model, and more particularly to producing a model with meta-learning on task sets for one population to produce a model for predicting the biological state of one person.

SUMMARY

In an aspect, the present disclosure provides a method for processing data sets. The method may comprise acquiring task data sets for users. The method may comprise training a model with each task data set to generate a task error value for the task set. The method may comprise generating a meta-error value from the task error values. The method may comprise generating meta-learned parameters for the model from the meta-error values. The method may comprise configuring the model with the meta-learned parameters. The method may comprise training the model configured with the meta-learned parameters with new user data to generate a trained model. The method may comprise inferring a biological response of the user with the trained model Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
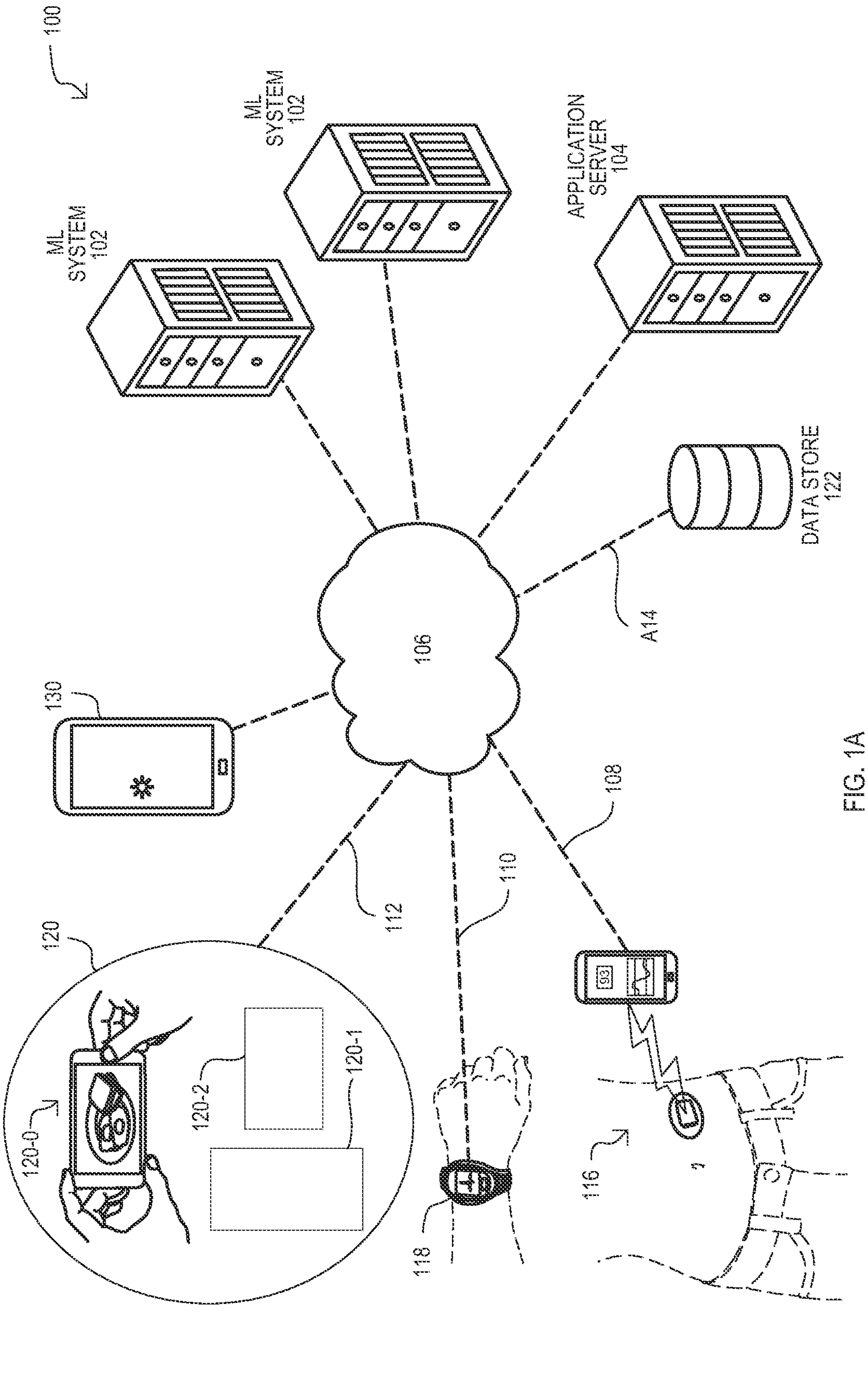
FIG. 1A is a diagram of a system according to an embodiment.

FIG. 1A shows a system 100 according to an embodiment. A system 100 can include one or more machine learning computing systems (e.g., servers) 102, application servers 104, data store 122, multiple data sources (108, 110, 112), which can provide task data sets, and subject devices 130. Data sources (108, 110, 112), servers (102, 104) and subject devices 130 can be in communication with one another, such as through a network 106, which can include various interconnected networks, including the internet.

Machine learning (ML) systems (102/104) can include various statistical models, including artificial neural networks (ANN) of various architectures, and related systems, as will be described herein and equivalents. Such systems can execute various functions, including meta-learning, learning and inference functions by using data received from data sources (116, 118, 120) and/or as well as other data residing on data storage 122. In some embodiments. ML systems (102/104) can include any suitable statistical learning agent, including any dimensionality reducer appropriate the domain and training data, such as autoencoders (AEs), as well as any of generative adversarial networks (GANs), long short-term memory networks (LSTMs), convolutional neural networks (CNNs), reinforcement learning (RL) algorithms, and any other ANN or related architecture suitable for the systems and methods described herein. ML systems (102/104) can include functions/models created by meta-learning which can be trained faster (e.g., with fewer iterations) than functions/models with random starting values.

An application server 104 can interact with one or more applications running on a subject device 130. In some embodiments, data from data sources (116, 118, 120) can be acquired via one or more applications on a subject device (e.g., smart phone) and provided to application server 104. Application server 104 can communicate with subject device 130 according to any suitable secure network protocol. Such communications can include recommendations as described herein and equivalents.

A data store 122 can store data for system 100. In some embodiments, data store 122 can store data received from data sources (116, 118, 120) (e.g., from subjects) as well as other data sets acquired by third parties. Such data can include task data sets used for meta-learning operations as will be described herein, or equivalents. Data store 122 can also store various other types of data, including ANN configuration data for configuring models ML systems (102/104). A data store 122 can take any suitable form, including one or more network attached storage systems. In some embodiments, all or a portion of data store can be integrated with any of the servers (102, 104).

In some embodiments, data for data sources (108, 110, 112) can be generated by sensors or can be logged data provided by subjects. In the example shown, data source 108 can correspond to a first type sensor 116, data source 110 can correspond to a second type sensor 118, and data source 112 can correspond to logged data 120 provided from a subject. Logged data 120 can include data from any suitable source including text data as well as image data.

According to some embodiments, a first type sensor 116 can be a "direct" data source, providing values for a biophysical subject response that can be predicted by the system 100. A second type sensor 118 and logged data 120 can be "indirect" data sources. Such "indirect" data sources can be provided as inputs to biophysical models of the system 120 to infer future a biophysical response different from the response(s) the second type sensor 118 records/detects. In some embodiments, both direct and indirect data can be used to train and calibrate biophysical models, however, direct data may not be used in inference operations in such embodiments. In some embodiments, a first type sensor 116 can be a sensor that is more difficult to employ than a second type sensor 118. While sensors (116, 118) can have data captured by a subject device A30, which can then send such data to servers (102/104), such sensors can also transmit such data to servers without a subject device (e.g., directly, or via one or more intermediate devices).

In particular embodiments, a first type sensor 116 can be a continuous glucose monitor (CGM), which can track a glucose level of a subject. A second type sensor 118 can be heart rate monitor (HRM) which can track a subject's heart rate. Logged data 120 can be subject nutrition data. In some embodiments, nutrition data 120 can be acquired by an application on a subject device 130. In some embodiments, image data can be captured, and such image data can be used as inputs to models on ML systems (102) to infer nutrition values. Image data can be images of text (e.g., labels 120-1) which can be subject to optical character recognition to generate text, and such text can be applied to an inference engine. In addition or alternatively, image data can be images of actual food (e.g., 120-0), or food packaging, and such image data can be applied to an inference engine. Further, logging can include capturing standardized labels (e.g., 120-2) which can be subject to a database search or ML model to derive nutrition values.

A subject device 130 can be any suitable device, including but not limited to, a smart phone, personal computer, wearable device, or tablet computing device. A subject device 130 can include one or more applications that can communicate with application server 122 to provide data to, and receive data from, biophysical models residing on ML systems 102. In some embodiments, a subject device 130 can be an intermediary for any of data sources (108, 110, 112).

Figure 1B:
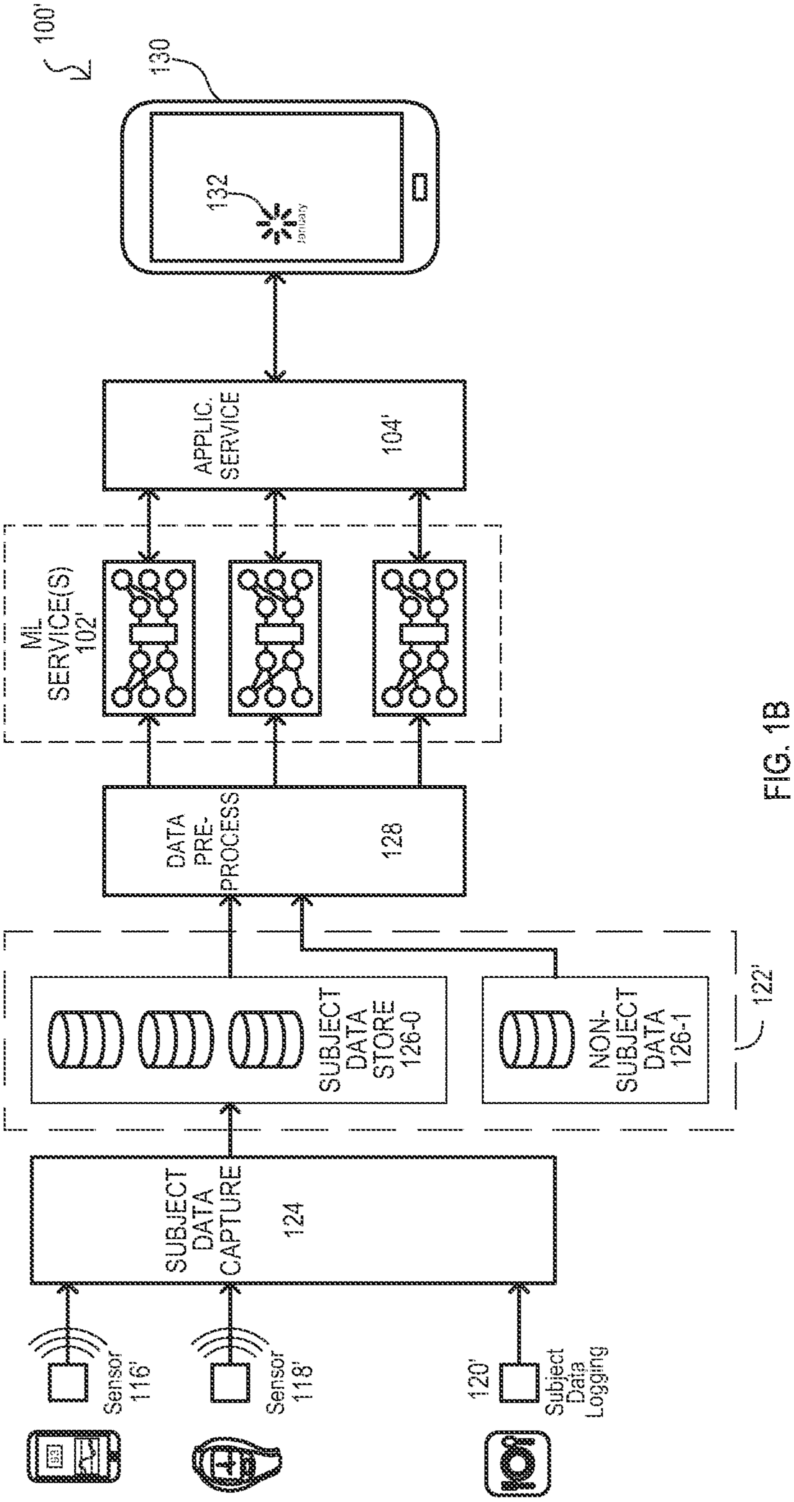
FIG. 1B is a diagram of a system according to another embodiment.

Referring to FIG. 1B, a system 100' according to another embodiment is shown in a block diagram. A system 100' can include data source inputs 116', 118', 120', a data subject capture portion 124, a storage portion 122', a data preprocessing portion 128, a ML services portion 102', and an application services portion 104'. Data source inputs (116', 118', 120') can provide data for learning operations in ML services 102' that create biophysical models for a subject and/or meta-learning operations that operate on disparate task sets. A portion or all of data source inputs (116', 118', 120') can provide data for training and/or inference operations executed on models resident in ML services portion 104'. In very particular embodiments, data source inputs (116', 118', 120') can include any of the sensors and/or subject data logging described herein or equivalents. As in the case of FIG. 1A, ML services 102' can generate and provide meta-learned models/functions generated with task sets of other users, that can be rapidly trained with data from a new user to arrive at a user customized function/model.

Data store portion 122' can include subject data storage 126-0 as well as non-subject data storage 126-1. Subject data storage 126-0 can be data for particular subjects for which ML models have been created or are being created, including trained with learning and meta-learning. Non-subject data storage 126-1 can include data derived from other sources that can serve as task sets for meta-learning purposes (e.g., data from other subjects, data form non-subjects, such as studies conducted by third parties).

A data pre-processing portion 128 can process data from data store portion 122' for application in ML services 102'. Data pre-processing portion 128 can include instructions executable by a processor to place data into particular formats for processing by ML services 102'.

ML services 102' can include computing systems configured to create ML models through supervised and/or unsupervised learning with any of data source inputs 116', 118', 120'. In addition, ML services 102' can create and include ML models that generate inferences based on any of data source inputs 116', 118', 120'. ML services 102' can include single computing devices that include ANNs of the various architectures described herein, as well as ANNs distributed over networks. As in the case of FIG. 1A, ML services 102' can include AEs, GANs, LSTMs, CNNs, RL algorithms, and any other suitable ANN or other statistical learning agent, and related architecture.

Application services 104' can access models/functions resident in ML services 102' to provide data for one or more subject applications 132. Applications 132 can utilize model outputs to provide information to subjects, including recommendations as described herein. In some embodiments, applications 132 can provide recommended actions for subjects based on subject responses predicted by models in ML services 102'. In some embodiments, applications 132 can recommend subject actions based on predicted glucose levels of subjects. In the embodiment shown, application services 104' can service applications 132 running on subject devices 130. However, in other embodiments application services 104' can execute applications and provide (e.g., push) data to other services (e.g., email, text, social network, etc.).

Figure 2:
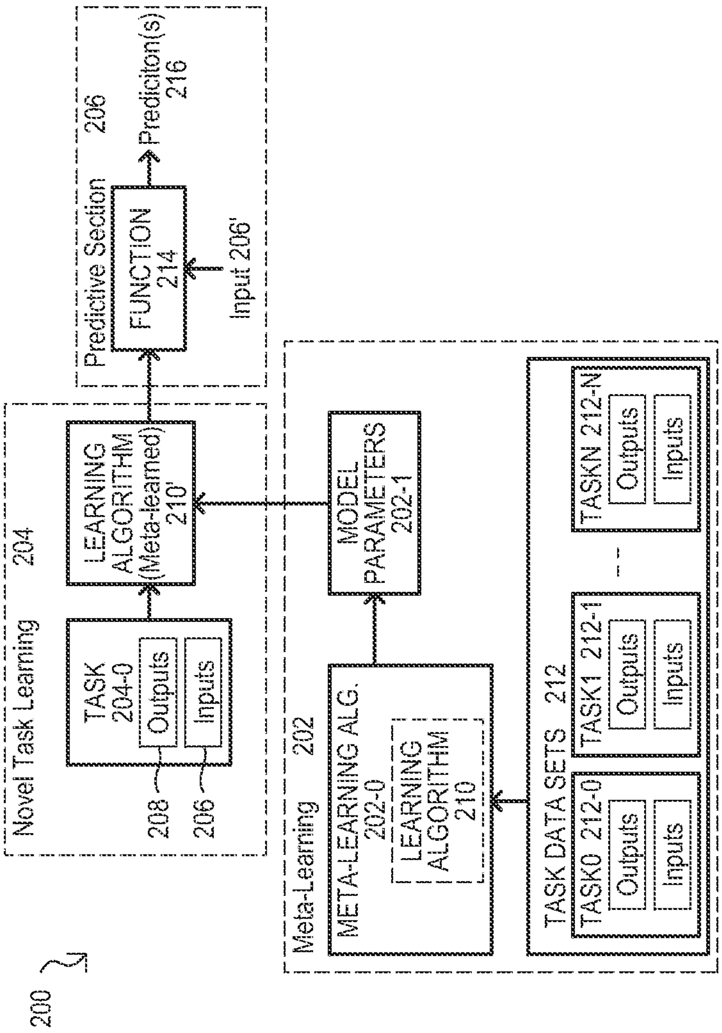
FIG. 2 is a diagram of a meta-learning system and method that can be included in embodiments.

FIG. 2 is a diagram of a meta-learning system 200 that can be included in embodiments. The meta-learning system 200 can generate starting model parameters to improve learning of a function, or enable learning on a function with less training (e.g., fewer training iterations). A system 200 can include a meta-learning section 202, a novel task learning section 204, and a predictive section 206. A meta-learning section 202 can execute a meta-learning operation to generate model parameters 202-1. A meta-learning section 202 can include a meta-learning function or algorithm 202-0 that can execute meta-learning with task data sets 212. A meta-learning algorithm 202-0 can execute meta-learning with a learning algorithm 210 to generate model parameters 202-1 for the learning algorithm 210. A learning algorithm 210 can correspond to that in novel task learning section 204. Model parameters 202-1 can include features of a model/function that can be adjusted in a learning operation to provide a desired model/function result.

A novel task learning section 204 can configure learning algorithm with model parameters 202-1 generated with meta-learning function 210'. Novel task learning 204 can then train on the learning algorithm 210" (with the meta-learned parameters) using new task data 204-0. New task data 204-0 may or may not correspond to a type of task in task data sets 212 used for meta-learning. New task data 204-0 can include input values 206 with corresponding output values 208. Such learning can take any suitable form that can further adjust parameters for the model/function of learning algorithm 210' based on error between input values 206 and output values 208. Following novel task learning section 204 can provide a function 214 for predictive section 206.

Predictive section 206 can include function 214 which can correspond to a model/function trained by novel task learning 204. Input values 206' can be applied to function 214 to generate one or more predicted outputs. In some embodiments, input values 206' can be from a same source as new task data 204-0 (e.g., from the same subject).

Figure 3:
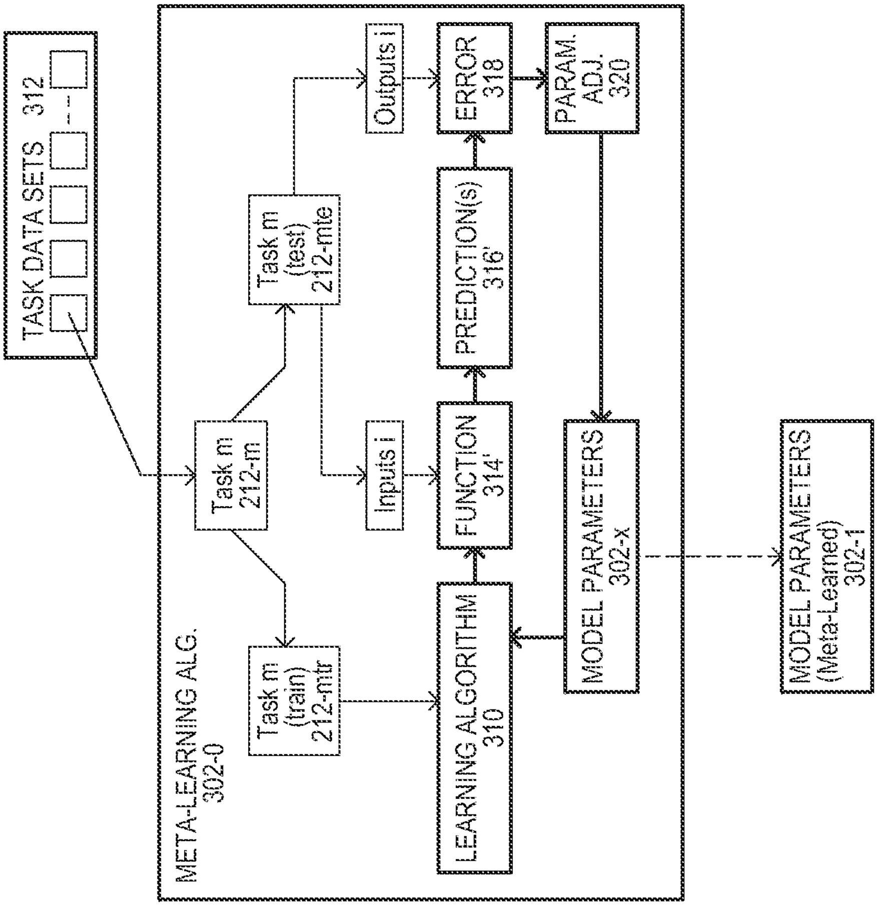
FIG. 3 is a block diagram of a meta-learning algorithm/function that can be included in embodiments.

FIG. 3 is a diagram showing a meta-learning algorithm (function) 302-0 that can be included in embodiments. Meta-learning algorithm 302-0 can include a learning algorithm 310, function 314', error function 318, parameter adjust function 320 and can generate predictions 316' and model parameters **302-*x*. Meta-learning algorithm 302-0 can iteratively pick a Task Data Set 212-*m* from the Task Data Sets 312, split the Task Data Set 212-*m* into a training set 212-*mtr* and a testing set 212-*mte*, and feed the training set 212-*mtr* to the Learning Algorithm 310, producing a Function 314'. The Function 314' can then be applied to generate predictions 316' in response to test set inputs. Such predictions 316' can be compared to corresponding test set output values, by error function 318. In response to an error value generated by error function, parameter adjust function 320 can generate modified model parameters 302-*x*. Such adjusted model parameters 302-*x* can be used by learning algorithm to adjust function 314'. At the same time, learning algorithm 310 can learn with its portion of the task data set 312. In this way, a meta-learning algorithm 302-0 can train (with learning algorithm 310) and test (with error function 318**) with each loop.

Such meta-learning can continue across various task data sets 312 (which can be for diverse tasks), with model parameters **302-*x* continuing to be adjusted in response to detected error between task data set inputs and outputs. Once learning has been executed with all task data sets 312, meta-learning algorithm 302-0 can result in model parameters 302-01**.

Figure 4A:
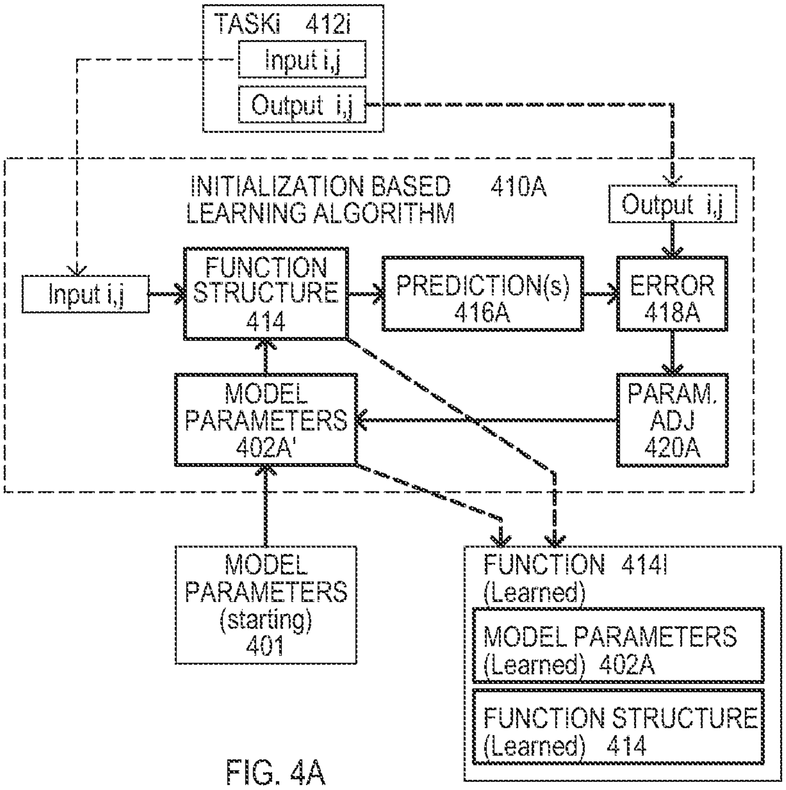
FIGS. 4A and 4B are diagrams of learning algorithms/functions that can be included in meta-learning algorithm/function functions according to embodiments.
Figure 4B:
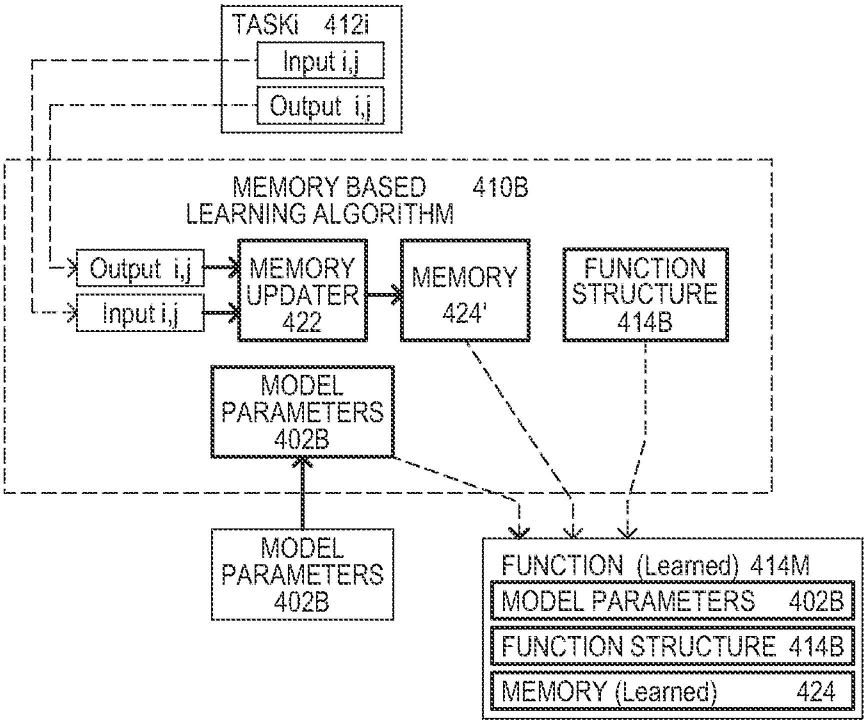

FIGS. 4A and 4B are diagrams of learning algorithms (functions) that can be included in embodiments. Such learning algorithms can correspond to those shown as 210 and 310 in FIGS. 2 and 3. That is, the learning algorithms of FIGS. 4A and 4B can be included in a meta-learning algorithm or operation.

FIG. 4A is a diagram of an "initialization" based learning algorithm (function) 410A. Algorithm 410A can include a function structure 414A', error function 418A, parameter adjusting function 420A. A function structure 414A' can generate predictions 416A from input values (input i,j) that will vary according to model parameters 402A'. Error function 418A can compare predictions 416A to corresponding output values (output i,j). Parameter adjusting function 420A can adjust model parameters 402A' based on error values. Consequently, a function structure 414A' response can be modified. In operation, function structure 414A' can be placed into an initial state with initial model parameters 401. Input values (input i, j) of task set **412*i* can be applied to function structure 414A', then via learning loop 416A, 418A, 420A, model parameters 402A' can be updated. Learning by initialization based learning algorithm 410A can arrive at a function 4141 that can include function structure 414 and model parameters 402**A generated through learning.

FIG. 4B is a diagram of a "memory" based learning algorithm (function) 410B. Algorithm 410B can include a memory updater 422, a memory function 424', and function structure 414B. A memory updater 422 can update a memory function 424' in response to input/output pairs (input i,j/output i,j) which can be from a task set **412*i*. In some embodiments, a function structure 414B and model parameters 402B can remain unchanged. Learning by memory based learning algorithm 410B can arrive at a function 414M that can include a memory function 424 (generated by operations of memory updater 422) function structure 414B and model parameters 402**B.

Figure 5:
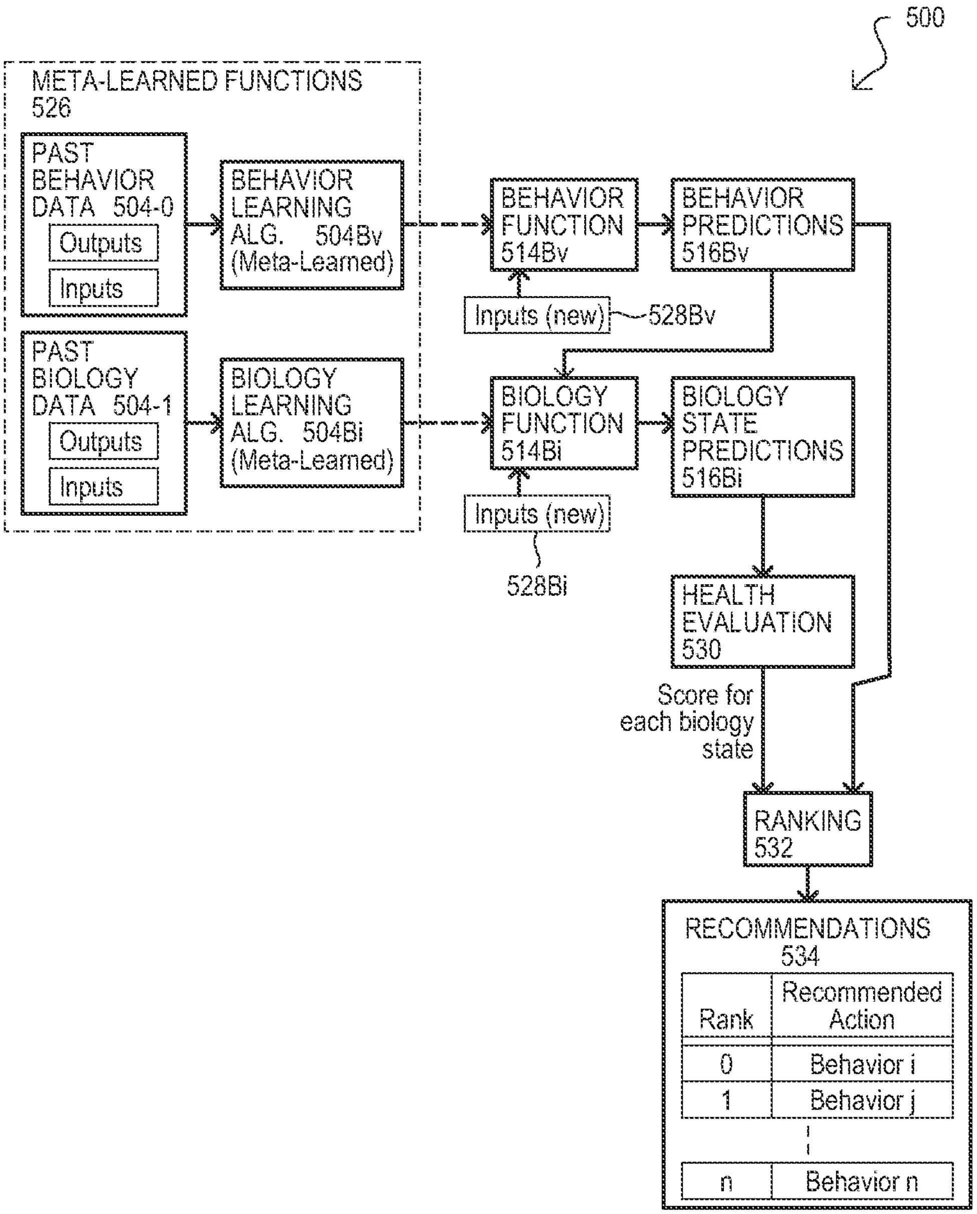
FIG. 5 is a block diagram of a recommendation system according to embodiments.

FIG. 5 is a block diagram of a recommendation system 500 according to embodiments. A system 500 may or may not include meta-learned functions 526, a behavior function 514Bv, a biology function 514Bi, health evaluation function 530 and ranking function 532. In response to inputs 528 for a user, a behavior function 514Bv can generate behavior predictions 516Bv. In response to inputs 528 for a user combined with each of the behavior predictions 516Bv for a user, a biology function 514Bi can generate biology state predictions 516Bi for each behavior prediction 516Bv.

Biology state predictions 516Bi can be subject to a health evaluation function 530. As but one example, a health evaluation function 530 can generate a health score for various predicted biology states. A ranking function 532 can rank various predicted behaviors 516Bv based on a corresponding health evaluation score. A ranking function 532 can generate recommendations based on a health evaluation score. It is note that such a ranking need not be based solely on a health evaluation score, but may take into account other factors (probability of behavior, as but one example).

It is understood that the various data sets and data input types shown in FIGS. 3, 4, and 5 can take the form of any of those described herein, or equivalents.

Embodiments can include other methods and systems for generating one or more personal recommendations for a subject based on a behavior model of the subject. A system can combine psychometric data with sensor and other data to provide contextual recommendation to a user.

Figure 6:
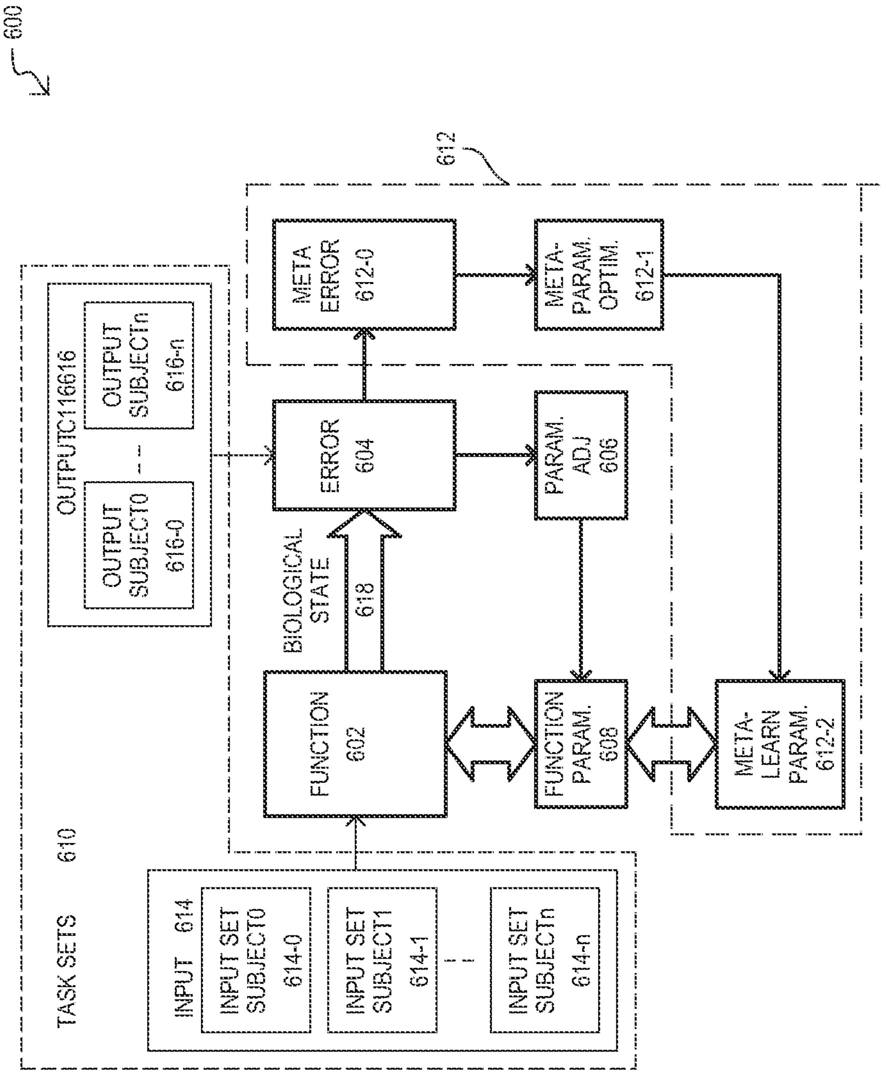
FIG. 6 is a block diagram of a system and method according to another embodiment.

FIG. 6 is a block diagram of a meta-learning system 600 and corresponding method according to an embodiment. A system 600 can include a configurable function 602, an error function 604, parameter adjustment function 606 and function parameters 608. In addition, a system 600 can include a meta-learning function 612 and task sets 610 of training data. A configurable function 602 can be a trainable statistical model that can generate one or more representations of biological states 618 in response to input data. Function 602 can vary a response according to function parameters 608. Function parameters 608 can include any function parameters that can be adjusted to converge output values on a desired (e.g., low error) distribution. In some embodiments, a function 602 can include a NN, and parameters can be neuron weights. In some embodiments, a function 602 can include a NN, and parameters can be neuron configurations (e.g., architecture, connections between neurons).

Error function 604 can generate an error value by comparing generated biological state values 618 to corresponding output values 616. A parameter adjustment function 606 can adjust function parameters in response to error data from error function 604 according to any suitable operation. In some embodiments, a parameter adjustment function 606 can include gradient descent operations to modify neuron weight values in response to error data.

Task sets 610 can include task data sets of subjects, including input data sets 614 and corresponding output data sets 616. In some embodiments, each task data set can include multiple training data sets and at least one test data set. In meta-learning operations, function 602 can be trained with training data sets and test data set(s) can be used to generate error values. In some embodiments, task data sets can be time series data. In some embodiments, task data sets correspond to different subjects and/or different actions of a subject.

Meta-learning functions 612 can include a meta-error function 612-0, a meta-parameter optimization function 612-1, and meta-learning parameter 612-2. A meta-error function 612-0 can generate meta-error values based on error values. Such meta-error values can take can form suitable for the meta-learning method. In some embodiments, meta-error can be based on an average, or weighted average of error values generated from task sets. Meta-parameter optimization function 612-1 can optimize parameters based on any method suitable for the model type. Meta-learning parameters 612-2 can be parameters developed through meta-learning operations that can be applied to function 602, to enable function 602 to rapidly learn from a novel data set.

Figure 7A:
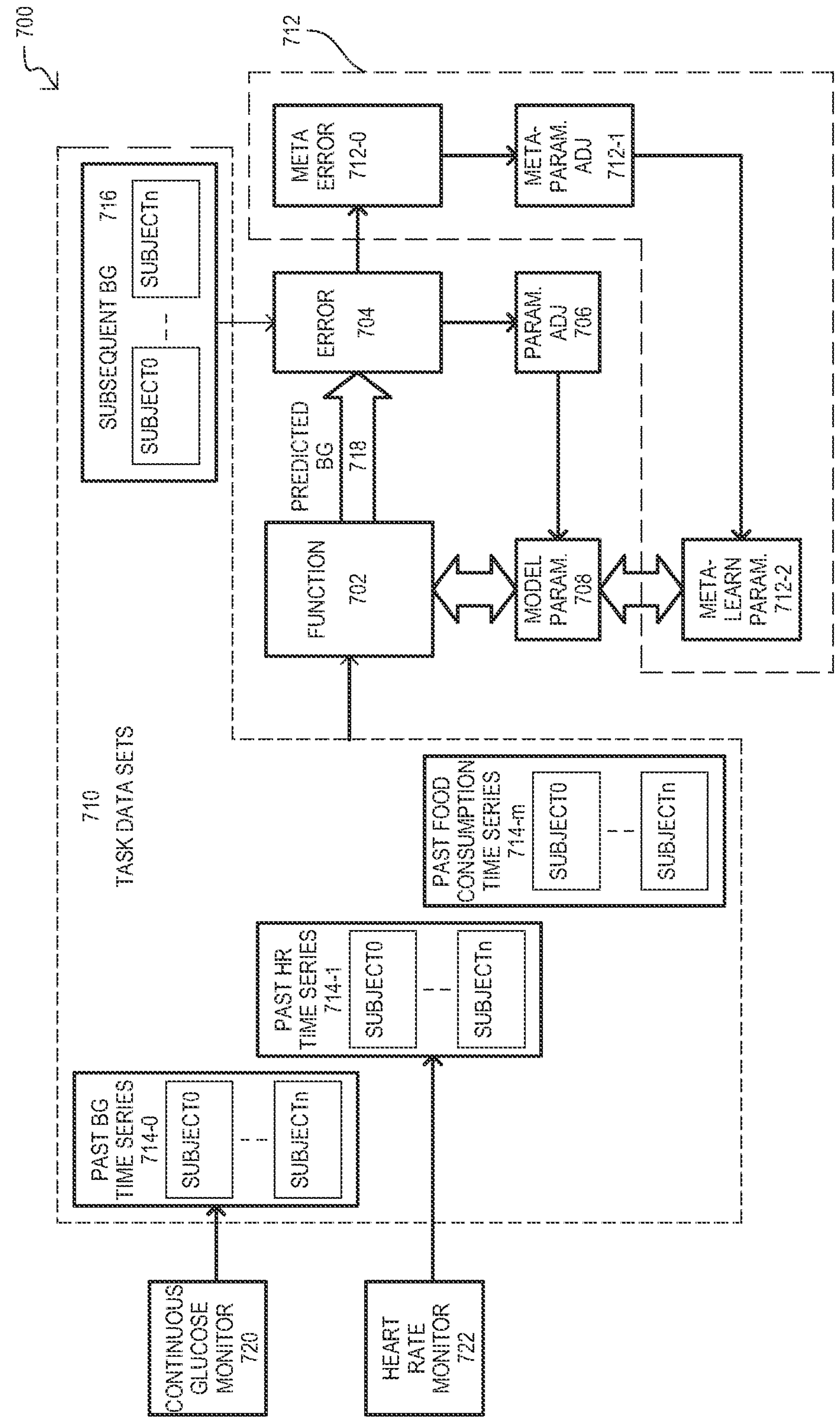
FIGS. 7A, 7B, 7C and 7D are diagrams of various systems and methods according to other embodiments.

FIG. 7A is a block diagram of a meta-learning system 700 and corresponding method according to an embodiment. System 700 can be one implementation of that shown in FIG. 6. Sensors can be used to generate task data sets. In the embodiment shown, glucose monitors 720 can generate blood glucose (BG) time series data 714-0/716 and heart rate monitors 722 can generate heart rate (HR) time series data 716. However, any suitable monitors can be used to generate task data sets. Task data 710 can also include food consumption data **714-*m*/716. Time series data can include data indicating an event or measurement (e.g., BG level, HR, food consumed) as well as the time (which can include date) at which the event/measurement took place. Task data sets 710** can include input as well as corresponding output data. In some embodiments, task data sets can include training data sets and at least one test data set.

Using time series data 710, function 702 can trained to infer a predicted BG response 718, and then to generate an error value with error function 704 which can rate the performance of the prediction. In a meta-learning operation, function 702 can be trained and tested with task data sets to generate error value for each task data set, and such error values can be used to generate a meta-error value with meta-error function 712-0. Based on a meta-error value, a meta-parameter optimization function 712-1 can adjust parameters of function to generate meta-learned parameters 712-2. Meta-learned parameters 712-2 can then be used to adjust function 702 for further meta-learning passes (i.e., task data sets can then be used once again to train and test function 702). A meta-error function 712-0 can determine when a meta-learning operation is complete according to any suitable method (e.g., minimized error, error within predetermined range).

In some embodiments, a function 702 can include a NN model having initial neuron weights. A system 700 can use meta-learning to generate initial weights for the NN model to rapidly arrive at a function 702 which can be quickly trained to provide a personalized model to predict the BG of a subject. Function 702 can be trained with task data sets, and a task error value generated for each task set. Meta-learning function 712 can generate meta-learned parameters based on meta-error. Such meta-learned parameters can serve an initial values for function 702. Additional passes can be made with the task data sets 710 until optimal meta-learned parameters are generated.

A meta-learning function 712 can optimize parameters according to any suitable method appropriate to the function 702 being used. Such methods can include but are not limited to the backpropagation of gradients, or meta-learning approaches directed to smaller task sets, such as LSTM meta-learning and model-agnostic meta-learning to name to two of many possible examples.

Figure 7B:
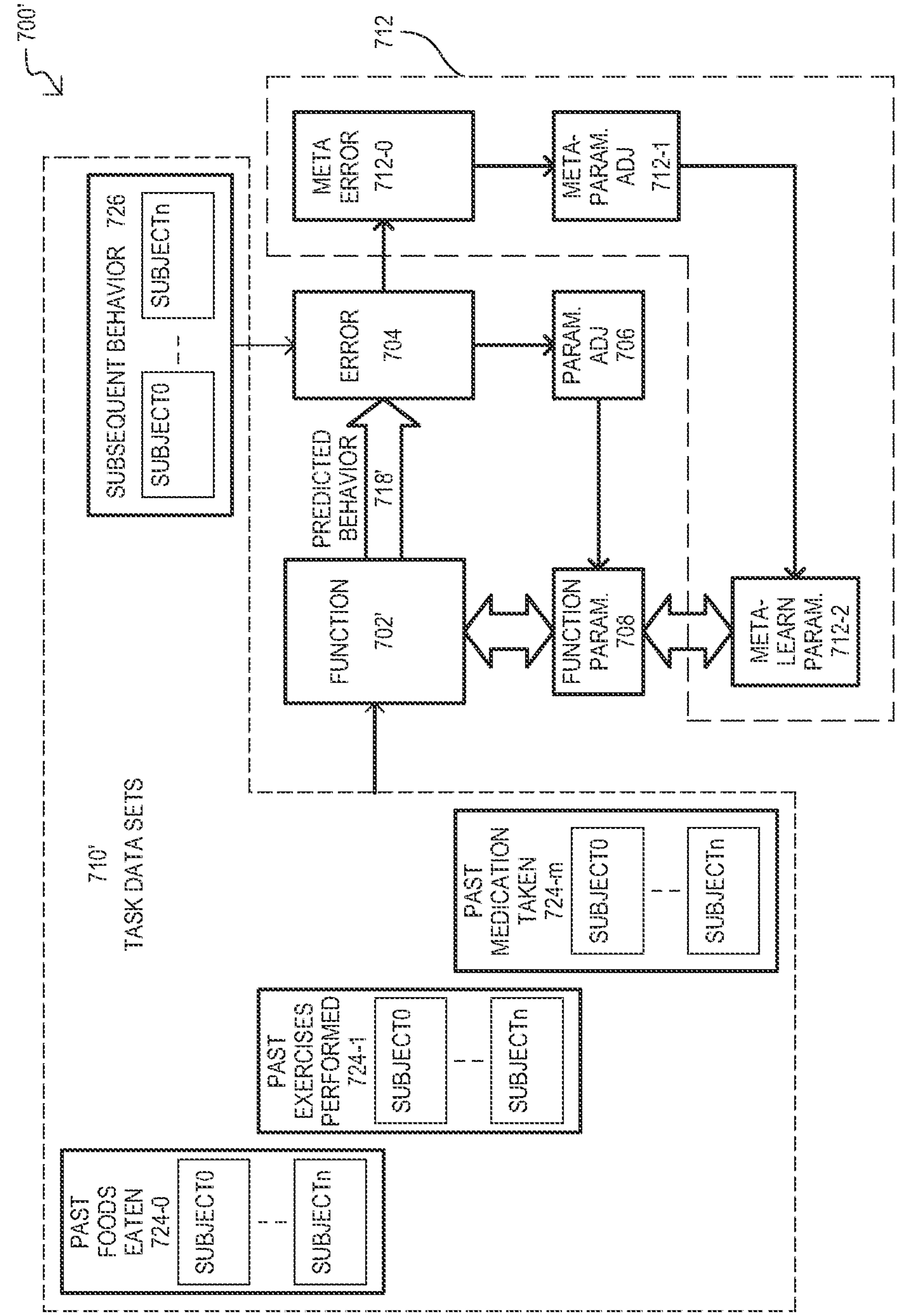

FIG. 7B is a block diagram of another system 700' and corresponding method according to another embodiment. A system 700' can include features like those of FIG. 7A, and such like features have the same reference character. A system 700' can differ from that of FIG. 7A in that task data sets 710' can include data on user behaviors, and can be used to generate parameters for function 702', which can predict user behavior. While user behavior task data can correspond to any suitable health-related behavior, in the embodiment shown, user behavior can include past foods eaten 724-0, past exercises performed 724-1, and past medication taken **724-*m***. Task data sets can include training data sets and at least one test data set.

In some embodiments, a system 700' can utilize meta-learning function 712 to optimize initial parameters for function 702'.

Figure 7C:
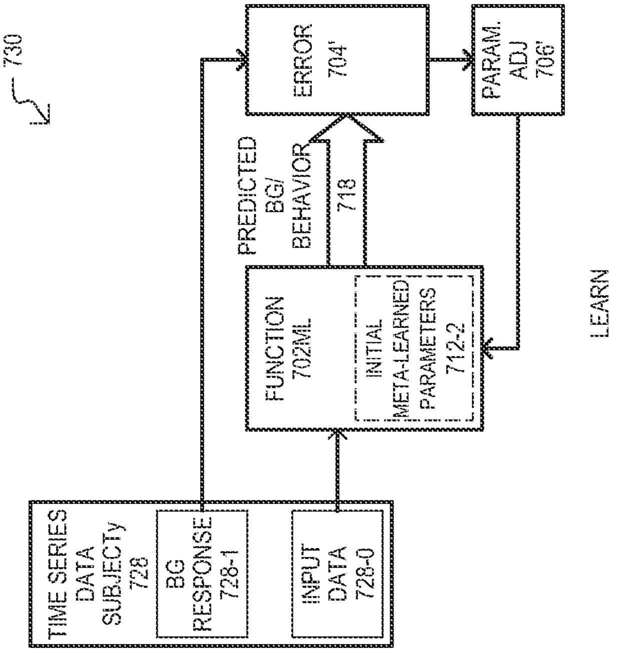

FIG. 7C is a block diagram showing a system 730 and corresponding method for training a meta-learned function 702ML with data for a new user. A new user can be a user whose data set was not used in a meta-learning operation. That is, function 702ML can have initial parameters 712-2 optimized through meta-learning with data sets of other users. In some embodiments, function 702ML can be a function like that of FIG. 7A and/or FIG. 7B, configured with meta-learned initial parameters.

New user data 728 can include input data 728-0 and output data 728-1. In some embodiments, input data 728-0 can include time series data for a user. In some embodiments, such time series data can correspond to one or more task data sets used in the meta-learning operation used to arrive at initial parameters 712-2 (e.g., BG, HR, food consumption, exercises performed, medication taken).

Figure 7D:
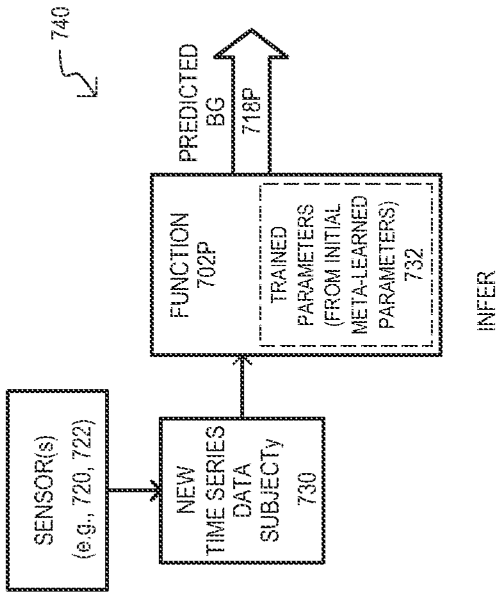

Function 702ML can be trained in any manner suitable for the function type, including backpropagation of gradients to generate modified (i.e., learned) parameters (indicated as 732 in FIG. 7D). Due to initial meta-learned parameters 712-2, a function 702ML can be trained to converge on a desired output response with a smaller data set, or smaller number of learning iterations. After training, function 702ML can be configured with learned parameters 732 optimized for the user. As such, function 702ML can be considered a function or model that is personalized to the user. In some embodiments, parameters 712-2/732 can include neuron weight values for layers of a NN included within function 702ML.

In some embodiments, function 102ML can correspond to that shown as 702/702' in FIGS. 7A and 7B.

FIG. 7D is a block diagram of a system 740 and corresponding method for inferring a user response 718P with a function 702P that has been optimized with meta-learning. A system 740 can include a function 702P configured with parameters 732 optimized for the user, as described for FIG. 7C.

New data from a user 730 can be applied to function 702P which can infer a user response 718P. In some embodiments, new data 730 can be generated from one or more sensors 720/722 (e.g., CGM, HRM). An inferred user response 718P can be a biological response, including predicted BG levels or a user behavior.

In some embodiments, function 702P can correspond to that shown as 702/702' in FIGS. 7A and 7B.

Figure 8A:
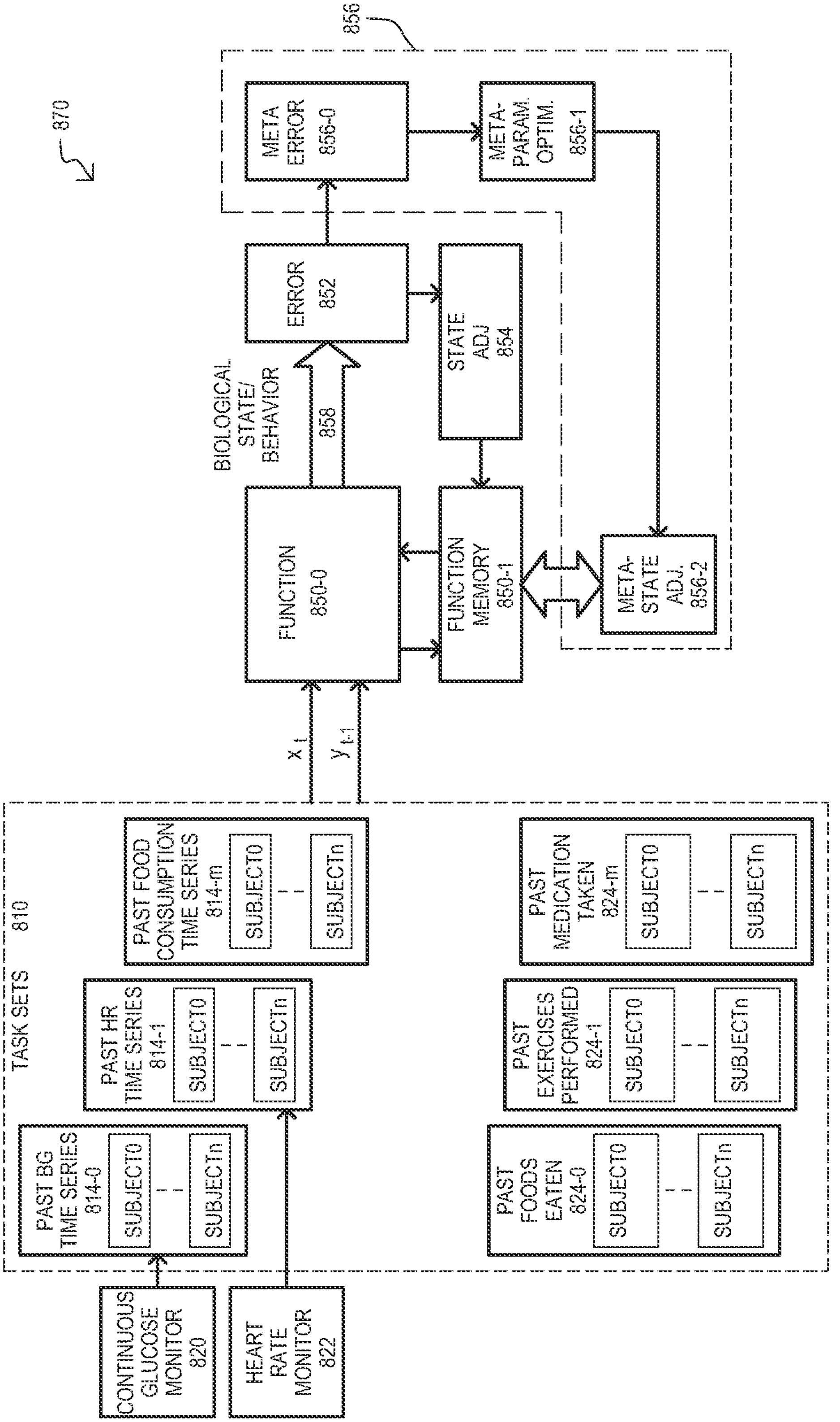
FIGS. 8A and 8B are diagrams of systems and methods according to further embodiments.

FIG. 8A is a block diagram of a meta-learning system 870 and corresponding method according to an embodiment. System 800 can be one implementation of that shown in FIG. 6. A system 800 can include task data sets 810, function 850-0, function memory 850-1, error function 852, state adjust function 854 and meta-learning function 856. Task data sets 810 can include those described for other embodiments herein, including task data sets 814-0 to *-m* for training to infer a biological response, such as BG levels, as well as task data sets 824-0 to *-m* for training to infer user behaviors.

According to embodiments, a function 850-0 can generate output values based on function memory 850-1 which can be modified as input and output data values are received. In some embodiments, a function 850-0 can receive both input and output values of task data sets. In some embodiments, there can be a step delay between input and output values (shown by input value $X_t$ received with output value $y_{t-1}$. Function 850-0 and corresponding memory 850-1 can be modified (e.g., optimized to minimize error) for each task data set, and then tested to generate a task error value by operation of task error function 852. Task errors values can be used meta-learning function 856 to generate a meta-error value 856-0. Based on a meta-error value an optimal meta-parameter adjustment can be generated 856-1, and function memory 850-1 can be updated 856-2 correspondingly.

Figure 8B:
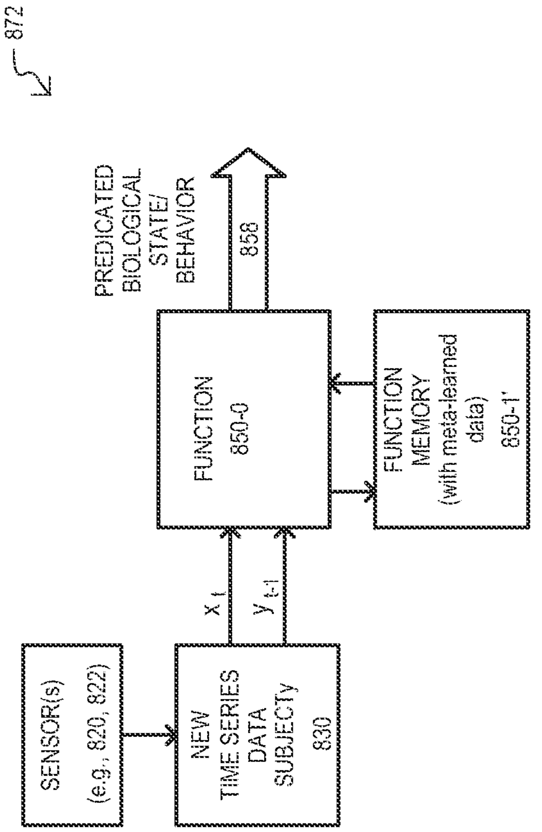

FIG. 8B is a block diagram of a system 872 and corresponding method for inferring a user response 858 with a function 850-0 and corresponding function memory 850-1 that has been optimized with meta-learning.

New data from a user 830 can be applied to function 850-0 which can infer a user response 858. In some embodiments, new data 830 can be generated from one or more sensors 820/822 (e.g., CGM, HRM). An inferred user response 858 can be a biological response, including predicted BG levels or a user behavior.

In some embodiments, function 850-0 and function memory 850-1 can correspond to that shown as 850/850-1 in FIG. 8A.

Figure 9:
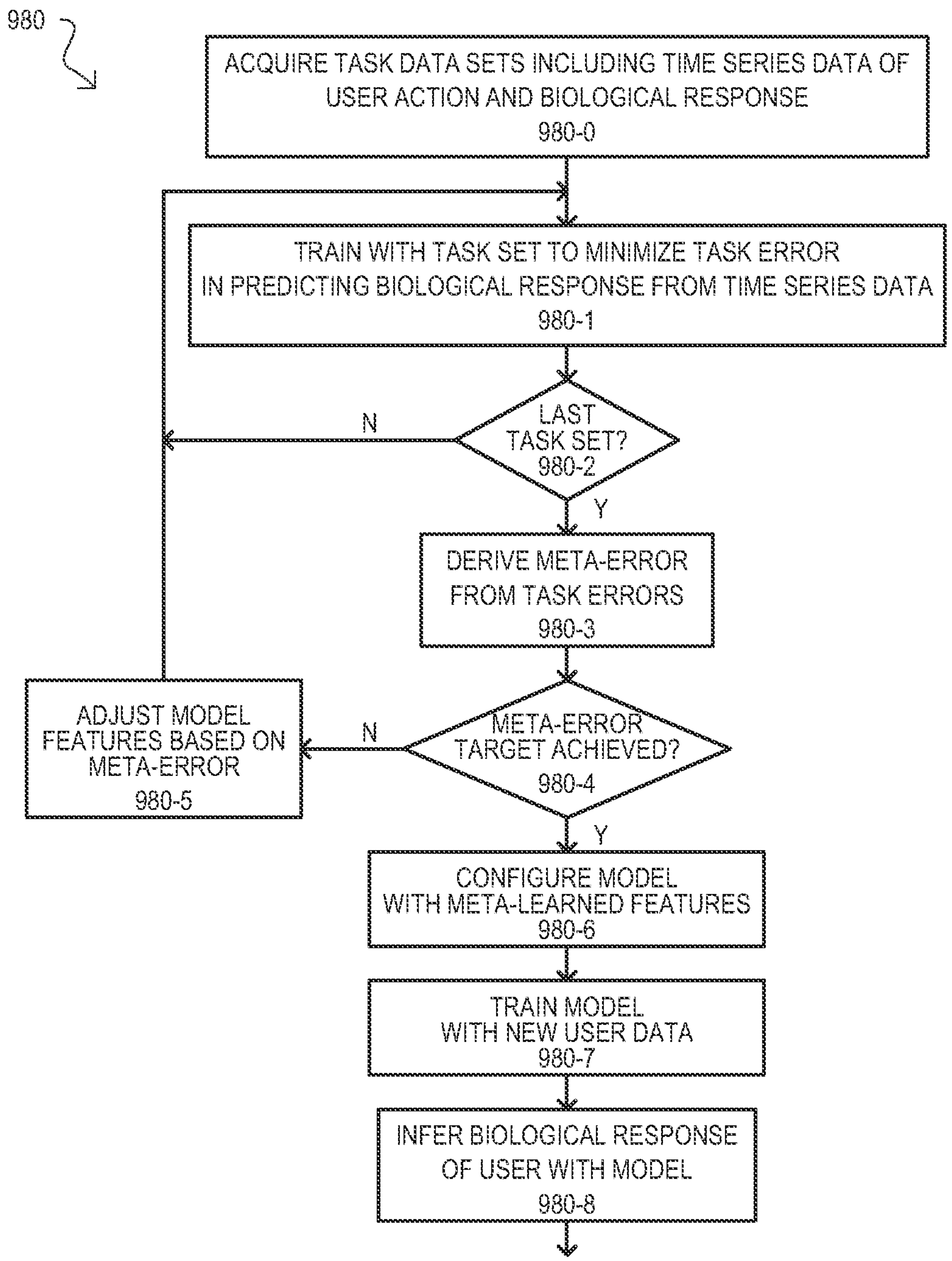
FIG. 9 is a flow diagram of a method according to an embodiment.

FIG. 9 is a flow diagram of a method 980 according to an embodiment. A method 980 can include acquiring task data sets including time series data of user actions can corresponding biological response 980-0. A model can be trained with a task set to minimize task error in predicting the biological response 980-1. Such an action can include generating a task error value for the task set. Once all task sets have been evaluated (Y from 180-2), a meta error value can be generated from the task set errors values 980-3. Until a meta-error target is achieved (i.e., minimized or below some predetermined threshold), model features can be adjusted 980-5, and a model can be trained with the task sets once again (return to 980-1). As but two of many possible examples, features can be initial weight values of a NN, or memory values of a memory based model.

When a meta-error target is achieved (Y from 980-4), a model can be configured with the meta-learned features 980-6. The configured model 980 can be trained with new user data 980-7. The trained model can then be used to infer a biological response of the user 980-8.

Computer Systems

Figure 10:
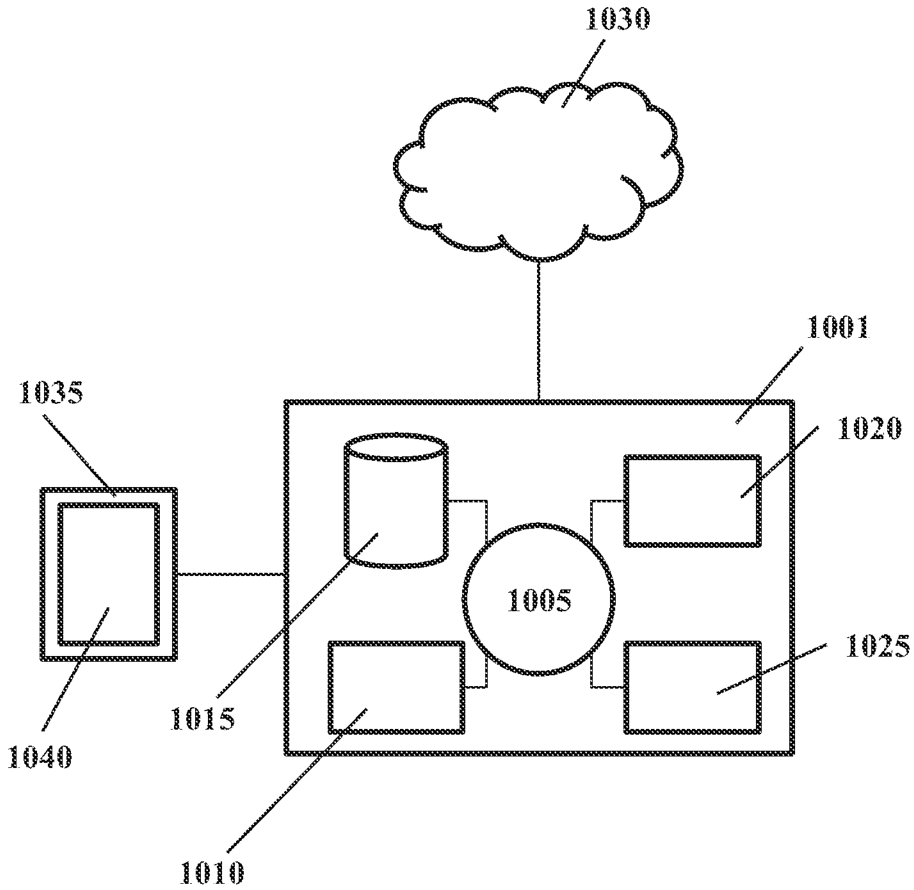
FIG. 10 schematically illustrates a computer system that is programmed or otherwise configured to implement methods provided herein.

In an aspect, the present disclosure provides computer systems that are programmed or otherwise configured to implement methods of the present disclosure. FIG. 10 shows a computer system 1001 that is programmed or otherwise configured to implement methods of the present disclosure. The computer system 1001 may be configured to, for example, acquire task data sets for users; train a model with each task data set to generate a task error value for the task set; generate a meta-error value from the task error values; generate meta-learned parameters for the model from the meta-error values; configure the model with the meta-learned parameters; train the model configured with the meta-learned parameters with new user data to generate a trained model; and infer a biological response of the user with the trained model. The computer system 1001 can be an electronic device of a user or a computer system that is remotely located with respect to the electronic device. The electronic device can be a mobile electronic device.

The computer system 1001 may include a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are located external to the computer system 1001 (e.g., on a remote server that is in communication with the computer system 1001 through an intranet or the Internet).

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, a portal for a user to view an inferred biological response of the user. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1005. For example, the algorithm may be configured to acquire task data sets for users; train a model with each task data set to generate a task error value for the task set; generate a meta-error value from the task error values; generate meta-learned parameters for the model from the meta-error values; configure the model with the meta-learned parameters; train the model configured with the meta-learned parameters with new user data to generate a trained model; and infer a biological response of the user with the trained model.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

It is understood that various blocks shown in the figures described herein can include any of various circuits configured to execute the indicated functions, including but not limited to servers systems that may or may not include customized hardware for accelerating operations, logic circuits, including custom logic circuits or programmable logic circuits. Such functions can also correspond to all or a portion of code executable by one or more processors that is stored on machine readable media. Data values as described herein can also be stored in machine readable media. Machine readable media can store code and/or data in a non-transitory form, in volatile and/or nonvolatile storage circuits.

It should be appreciated that in the foregoing description of exemplary embodiments of the invention, various features of the invention are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

It is also understood that the embodiments of the invention may be practiced in the absence of an element and/or step not specifically disclosed. That is, an inventive feature of the invention may be elimination of an element.

According to embodiments, blocks or actions that do not depend upon each other can be arranged or executed in parallel.

Accordingly, while the various aspects of the particular embodiments set forth herein have been described in detail, the present invention could be subject to various changes, substitutions, and alterations without departing from the spirit and scope of the invention.

What is claimed is:

1. A method for personalized blood glucose monitoring for a test subject, comprising:

(a) acquiring a plurality of task data sets from a plurality of subjects, each of the plurality of task data sets comprising input values and output values from a different source associated with a subject in the plurality of subjects, wherein the acquiring comprises (i) using a continuous glucose monitor (CGM) sensor to obtain time-series blood glucose measurements of the subject, and (ii) using a heart rate monitor (HRM) sensor to obtain time-series heart rate monitor values of the subject;

wherein the task data sets comprise time series data, with a value for one time being an input value, and a value for a subsequent time being an output value;

(b) performing a meta-learning operation comprising:

(1) processing at least a portion of the input values with a biology model that generates predicted output values comprising at least one blood glucose level corresponding to the input values, wherein the biology model comprises a neural network configured to process the time series data, such that a value for one time of the time series data is processed as an input value to the neural network and another value for a subsequent time of the time series data is produced as an output value of the neural network, (2) generating meta-learning error values at least in part by comparing each predicted output value to the output value corresponding to the respective input value, (3) training the biology model based at least in part on the meta-learning error values, wherein the training comprises adjusting parameters for the neural network of the biology model, such that the biology model reaches convergence with a meta-error target of the biology model, wherein the parameters are stored as meta-learned parameters after all task data sets have been processed by the meta-learning operation;

(c) training a population-based meta-learned model, at least in part by configuring the neural network of the biology model with the meta-learned parameters;

(d) acquiring test subject data from the test subject by (i) using the CGM sensor to obtain time-series blood glucose measurements of the test subject, and (ii) using the HRM sensor to obtain time-series heart rate monitor values of the test subject, wherein the test subject data was not used for performing the meta-learning operation in (c), and wherein the test subject is not among the plurality of subjects in (a); and (e) subsequent to the training of (c), training a personalized subject prediction model to predict at least one blood glucose level for the test subject, at least in part by re-training the population-based meta-learned model with the test subject data, the test subject data set comprising input values and output values and being different from each of the task data sets, wherein the re-training comprises adjusting the meta-learned parameters of the population-based meta-learned model, such that the personalized subject prediction model reaches convergence with an error target of the personalized subject prediction model, thereby producing a personalized subject prediction model that is optimized for the test subject; and (f) predicting a blood glucose level for the test subject with the personalized subject prediction model.

2. The method of claim 1, wherein the task data sets comprise food consumption events.

3. The method of claim 1, wherein the task data sets comprise data for different populations.

4. The method of claim 1, wherein the test subject data set comprises time series data, with a value for one time being an input value, and a value for a subsequent time being an output value corresponding to the input value.

5. The method of claim 1, wherein the neural network comprises a long short-term memory network (LSTM).

6. A method for personalized behavior monitoring of a test subject, comprising:

(a) acquiring a plurality of task data sets from a plurality of subjects, each of the plurality of task data sets comprising input values and output values of human behaviors from a different source associated with a subject in the plurality of subjects, wherein the acquiring comprises (i) using a continuous glucose monitor (CGM) sensor to obtain time-series blood glucose measurements of the subject, and (ii) using a heart rate monitor (HRM) sensor to obtain time-series heart rate monitor values of the subject;

wherein the task data sets comprise time series data, with a value for one time being an input value, and a value for a subsequent time being an output value;

(b) performing a meta-learning operation comprising:

(1) processing at least a portion of the input values with a behavior model that generates predicted output values comprising at least one behavior corresponding to the input values, wherein the behavior model comprises a neural network configured to process the time series data, such that a value for one time of the time series data is processed as an input value to the neural network and another value for a subsequent time of the time series data is produced as an output value of the neural network, (2) generating meta-learning error values at least in part by comparing a predicted output value to the output value corresponding to the respective input value, (3) training the behavior model based at least in part on the meta-learning error values, wherein the training comprises adjusting parameters for the neural network of the behavior model, such that the behavior model reaches convergence with a meta-error target of the behavior model, wherein the parameters are stored as meta-learned parameters after all task data sets have been processed by the meta-learning operation;

(c) training a population-based meta-learned model, at least in part by configuring the neural network of the behavior model with the meta-learned parameters;

(d) acquiring test subject data from a test subject by (i) using the CGM sensor to obtain time-series blood glucose measurements of the test subject, and (ii) using the HRM sensor to obtain time-series heart rate monitor values of the test subject, wherein the test subject data was not used for performing the meta-learning operation in (c), and wherein the test subject is not among the plurality of subjects in (a);

(e) subsequent to the training of (c), training a personalized subject prediction model for the test subject to predict at least one behavior for the test subject, at least in part by re-training the population-based meta-learned model with test subject data set, the test subject data set comprising input values and output values and being different from each of the task data sets, wherein the re-training comprises adjusting the meta-learned parameters of the population-based meta-learned model, such that the personalized subject prediction model reaches convergence with an error target of the personalized subject prediction model, thereby producing a personalized subject prediction model that is optimized for the test subject; and (f) predicting a behavior of the test subject with the personalized subject prediction model.

7. The method of claim 6, wherein the task data sets comprise food consumption events.

8. The method of claim 6, wherein the task data sets comprise physical activities.

9. The method of claim 6, wherein the task data sets comprise population data.

10. The method of claim 6, wherein predicting the predicted behavior comprises a plurality of behaviors.

11. The method of claim 6, wherein the predicted behavior comprises at least one food consumption event.

12. The method of claim 6, wherein the predicted behavior comprises at least one physical activity.

13. The method of claim 6, wherein the neural network comprises a long short-term memory network (LSTM).

* * * * *